United States Patent
Nakamura et al.

(12) 
(10) Patent No.: US 6,303,126 B1
(45) Date of Patent: *Oct. 16, 2001

(54) TREATMENT OF FIBROSIS BY HGF

(75) Inventors: Toshikazu Nakamura, 10-27, Takamidai, Takatsuki-shi, Osaka 569; Akira Shiota; Nobuaki Fujise, both of Shimotsuga-gun; Mitsuo Namiki, Takarazuka, all of (JP)

(73) Assignees: Toshikazu Nakamura, Osaka; Snow Brand Brand Milk Products Co., Ltd, Hokkaidou; Sumitomo Pharmaceuticals Co., Ltd., Osaka, all of (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/072,742

(22) Filed: May 6, 1998

Related U.S. Application Data

(62) Division of application No. 08/732,332, filed on Dec. 11, 1996, now Pat. No. 5,840,311.

(30) Foreign Application Priority Data

Apr. 28, 1994 (JP) .................................................. 6-114372

(51) Int. Cl.⁷ .................................................. A61K 38/18
(52) U.S. Cl. .............................. 424/198.1; 514/12; 514/2; 514/8
(58) Field of Search ........................... 424/198.1; 514/12, 514/2, 8

(56) References Cited

U.S. PATENT DOCUMENTS 5,004,805   4/1991  Gohda et al. .
5,840,311 * 11/1998 Nakamura et al. .

FOREIGN PATENT DOCUMENTS

0456188  * 11/1991 (EP) .
0462549A1  12/1991 (EP) .

OTHER PUBLICATIONS

M. Odenthal et al., Pathology Research and Practice, 190(3) pp. 238–239 (1994) XP002123899.
Chemical Abstracts, 122(15) (1995).
Chemical Abstracts, 171(14) pp. 1088–1092 (1994).
Garabedian et al., Circulation, 92(8) pp. 1750 (1995) XP002022818.
Igaku No. Ayumi, (171)14 pp. 1083–1087 (1994).
Wahl et al Journal of Immunology vol. 121, No. 3, Sep. 1978 pp. 942–946.*
Shiota et al., *Hepatol.*, 21:106–12 (1995).
Gherardi et al., *Proc. Natl. Acad. Sci.*, 86:5844–48 (Aug. 1989).
Shimizu et al., *J. Biochem*, 109:14–18 (1991).
Ishiki et al., *Hepatol.*, 16:1227–35 (1992).

* cited by examiner

*Primary Examiner*—Geetha P. Bansal
(74) *Attorney, Agent, or Firm*—Birch, Stewart, Kolasch, & Birch, LLP.

(57) ABSTRACT

The present invention relates to a method for treating fibrosis caused by excessive collagen deposition. The method involves administering Hepatocyte Growth Factors (HGFs). The HGFs accelerate the decomposition of the collagen when administered in an effective amount.

1 Claim, 6 Drawing Sheets

HGF (μg/kg/day, twice a day, IV)

- ■ SOLVENT ADM. GROUP
- ▨ HGF (100 μg/kg/day) ADM. GROUP
- ▨ HGF (1000 μg/kg/day) ADM. GROUP
- ▨ NORMAL ANIMALS DURATION OF TREATMENT (days)

NORMAL RATS   PHYSIOLOGICAL SALINE   HGF (50 μg/kg BW)   HGF (200 μg/kg BW)

TREATMENT OF FIBROSIS BY HGF

This application is a divisional of application Ser. No. 08/732,332, filed on Dec. 11, 1996 now U.S. Pat. No. 5,840,311. Application Ser. No. 08/732,332 is the national phase of PCT International Application No. PCT/JP95/00822 filed on Apr. 25, 1995 under 35 U.S.C. § 371. The entire contents of each of the above identified applications are hereby incorporated by reference.

TECHNICAL FIELD

The present invention relates to an agent accelerating collagen decomposition and a therapeutic agent for fibrosis disorder. More particularly, the present invention relates to an agent accelerating collagen decomposition and a therapeutic agent for fibrosis disorder comprising HGFs (Hepatocyte Growth Factors) as an active ingredient.

BACKGROUND ART

Fibrosis is a disease characterized by the excessive accumulation of a connective tissue component, and one which is a noticeable component in fibrosis is collagen.

Accumulation of collagen occurs in a variety of viscera, for example, brings about pulmonary fibrosis in lung and liver fibrosis in liver. Also in skin, for example, the accumulation of collagen brings about disorders such as cutis keloid formation.

In many cases, the net accumulation of collagen in fibrosis is the result of disproportion between factors which bring about decomposition and production of collagen.

Though various medications have been conducted to treat the disorder and sickness of fibrosis, they were mainly for symptomatic therapy for the disorder in general, and were not those which aim at dissolving pathogenesis, namely the disproportion between metabolism factors which regulate decomposition and production of collagen and the other connective tissue component. Therefore, in these therapies, there was no especially effective method in point of tissue repair. For example, though local corticosteroid was used to treat the initial inflammation stage of cutis keloid formation and success was made to a certain extent, such steroid treatment has little or no effect on the latter fibrosis stage such as in case of actual formation of keloid as a result of excessive production of collagen.

As described above, in the prior art, there could not have been discovered a safe and effective method which treats fibrosis disorder of human, inhibits more formation of fibrous tissue and reduces or completely removes the focus of fibrosis previously formed.

The object to be solved by the present invention is to provide an agent accelerating collagen decomposition which can induce the decomposition of a collagen matrix of excessively accumulated connective tissue in tissue and a therapeutic agent useful for treatment of fibrosis disorder.

DISCLOSURE OF THE INVENTION

The present inventors have intensively investigated to solve the object described above, As a result, the inventors found that HGFs have an action to promote the decomposition of collagen and are effective for the treatment of fibrosis disorder based on their action. And thereby the present invention has been completed.

Namely, the present invention is an agent accelerating collagen decomposition containing at least one of HGFs as an active ingredient.

Another invention is a therapeutic agent for fibrosis disorder containing at least one of HGFs as an active ingredient.

Still other inventions are a method for accelerating collagen decomposition comprising administering at least one of HGFs in an effective amount; a method for treating fibrosis disorder comprising administering at least one of HGFs in an effective amount; use of at least one of HGFs for producing an agent accelerating collagen decomposition; and use of at least one of HGFs for producing a therapeutic agent for fibrosis disorder.

BRIEF DESCRIPTION OF THE DRAWINGS

In FIG. 6, the dotted line indicates a group (control group, n=10) receiving physiological saline, the broken line indicates a group (n=5) receiving HGF at a dose of 50 μg/kg body weight, and the solid line indicates a group (n=5) receiving HGF at a dose of 200 μg/kg body weight.

FIG. 7A, normal rats; FIG. 7B, saline-treated rats; FIG. 7C, rats treated with HGF at 50 μg/kg; FIG. 7D, rats treated with HGF at 200 μg/kg.

BEST MODES OF CARRYING OUT THE INVENTION

Figure 1:
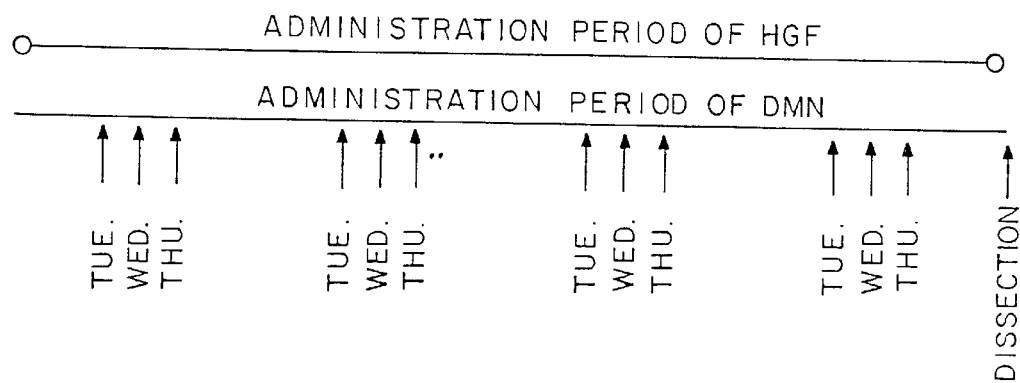
FIG. 1 is a chart which shows medicine-administration schedule in Example 1.

In the present invention, the term HGFs indicate proteins which exhibit hepatocyte growth activity, and HGF (Hepatocyte Growth Factor) and the like are exemplified.

As the HGFs used in the present invention, compounds prepared by various methods can be used if they are purified to an extent that they may be used as a medicine.

Many methods are known to prepare HGFs, and, for example, HGF can be obtained by extraction and purification from organs such as liver, spleen, lung, bone marrow, brain, kidney, placenta and the like, blood cells such as platelets, leukocytes and the like, plasma and serum of mammals such as rat, cow, horse, sheep and the like (FEBS Letters, 224, 311–316, 1987; Proc. Natl. Acad. Sci. USA, 86, 5844, 1989).

Also, it is possible to obtain HGF by cultivation of primary culture cells or cell lines producing HGF, followed by separation and purification from the culture product (e.g. culture supernatant, cultured cell, etc.). Further, HGF can be obtained by gene engineering method which comprises cloning the gene encoding HGF, inserting it into a suitable vector, transfecting the vector to obtain a transformant, and isolating the aimed recombinant HGF from the culture supernatant of the transformant (e.g. Nature, 342, 440, 1989; Biochem. Biophys. Res. Commun., 163, 967, 1989). The host cell is not specifically limited, and various host cells conventionally used in gene engineering methods can be used, which are, for example, Escherichia coli, Bacillus subtilis, yeast, filamentous fungi, and plant or animal cells.

More concretely, the method of extracting and purifying HGF from fresh tissues is, for example, to administer carbon tetrachloride to a rat intraperitoneally, remove a liver from the rat with hepatitis, homogenize it, and purify by the ordinary protein purification techniques such as gel column chromatography using S-Sepharose and heparin Sepharose, HPLC and the like.

Further, using the gene engineering method, the gene encoding the amino acid sequence of human HGF is inserted into a vector such as bovine papilloma virus DNA and the like to obtain an expression vector, by using this expression vector, animals cells such as Chinese hamster ovary (CHO) cells, mouse C127 cells, monkey COS cells and the like are transformed, and HGF can be obtained from the culture supernatant of the transformants.

As to HGFs thus obtained, there are possibilities that a part of the amino acid sequence of HGFs will be deleted or substituted with other amino acid(s), that another amino acid sequence is partially inserted, that one, two or more amino acids are attached to the C and/or N terminals, or that sugars are similarly deleted or substituted.

The agent accelerating collagen decomposition of the present invention comprises the above-described HGFs as an active ingredient, and the HGFs have accelerating action for collagen decomposition (increase of collagenase activity) as shown in the test examples mentioned later. Therefore, the agent accelerating collagen decomposition of the present invention is effective for the treatment of the following fibrosis disorder as well as the prevention thereof, and useful for the treatment and prevention of a disease due to reduced collagenase activity, for example, osteopetrosis or the like.

Further, the therapeutic agent for fibrosis disorder of the present invention likewise comprises the above-described HGFs as an active ingredient, and is useful for the treatment of the fibrosis disorders characterized by excessive production of fibroblast-derived connective tissue matrix containing collagen, fibronectin and glycosaminoglycan (GAG). They include the following disorders.

Arterial sclerosis, chronic glomerulonephritis, cutis keloid formation, progressive systemic sclerosis (PSS), liver fibrosis, pulmonary fibrosis, cystic fibrosis, chronic graft versus host disease, scleroderma (local and systemic), Peyronie's disease, penis fibrosis, urethrostenosis after the test using a cystoscope, inner accretion after surgery, myelofibrosis, idiopathic retroperitoneal fibrosis.

The agent accelerating collagen decomposition and the therapeutic agent for fibrosis disorder of the present invention are applicable to the treatment of fibrosis disorder and the acceleration of collagen decomposition in mammals (for example, cow, horse, pig, sheep, dog, cat and the like) in addition to human.

The agent accelerating collagen decomposition and therapeutic agent for fibrosis disorder of the invention may be prepared in various preparation forms (for example, liquid, tablet, capsule), and generally it is prepared in the form of injection, inhalation, suppository or oral preparation containing HGFs as the active ingredient alone or together with conventionally used carrier. The injection may be prepared by the conventional method, and for example, HGF is dissolved in a proper solvent (for example, sterilized water, buffer solution, physiological saline), filtered and sterilized, and put in a container aseptically. The content of HGF in the injection may be usually 0.0002 to 0.2 w/v %, preferably 0.001 to 0.1 w/v %. As the oral preparation, it is manufactured in various preparation forms, including tablet, granule, fine granule, powder, soft or hard capsule, liquid, emulsion, suspension or syrup, and these preparations may be manufactured by the conventional method. As to the suppository, it can be prepared by the conventional pharmaceutical method using a suppository base (for example, cacao oil, laurin oil, glycero-gelatin, macrogol, witepsol, etc.). Further, as to the inhalation, it also can be prepared by the conventional pharmaceutical method. The HGFs content in the preparation may be properly adjusted depending on the preparation form and the disease to be treated.

In production of the preparation, it is preferable to add a stabilizer, and examples of the stabilizer include albumin, globulin, gelatin, glycine, mannitol, glucose, dextran, sorbitol, ethylene glycol and the like. Moreover, the preparation of the invention may contain other additives necessary for pharmaceutical preparation, such as an excipient, a dissolving aid, an antioxidant, a pain-alleviating agent, an agent for isotonicity and the like. In liquid preparation, it is preferable to store it under frozen conditions or after the removal of water by a process such as lyophilization. The lyophilized preparation is used by dissolving again in distilled water for injection and the like before use.

The agent accelerating collagen decomposition and therapeutic agent for fibrosis disorder of the invention are administered through various routes depending on the preparation form. For example, the injection is administered by intravenous, intraarterial, subcutaneous, intramuscular and the like. The dose is adjusted properly depending on symptoms, age and body weight of patient, and generally 0.05 mg to 500 mg, preferably 1 mg to 100 mg of HGFs is administered once or several times per day.

Industrial Applicability

HGFs, the active ingredients of the present invention, accelerate the decomposition of collagen (increase of collagenase activity), and can effectively treat fibrosis disorder. Therefore, according to the present invention, the prevention and treatment of a disease due to reduced collagenase activity (for example, osteopetrosis or the like) and the above-described fibrosis disorders characterized by excessive production of fibroblast-derived connective tissue matrix are possible.

EXAMPLES

The present invention is illustrated in detail with reference to the following Preparation Examples and Examples, which should not be construed as limiting the scope the present invention.

Preparation Example 1

| Production example of HGF formulation | | |
|---|---|---|
| (1) | HGF | 20 μg |
| | Human serum albumin | 100 mg |

The above-described substances were dissolved in 0.01 M of PBS (pH 7.0), and the resulted solution was filled up to 20 ml with the same solvent. The resulting mixture was sterilized, then 2 ml aliquots of the mixture were poured into vials separately and they were lyophilized and sealed.

| (2) | HGF | 40 µg |
|---|---|---|
|  | Tween 80 | 1 mg |
|  | Human serum albumin | 100 mg |

The above-described substances were dissolved in a physiological saline for injection to prepare a mixture having a total volume of 20 ml. The resulting mixture was sterilized, then 2 ml aliquots of the mixture were poured into vials separately and they were lyophilized and sealed.

Example 1

Preventing and Improving Effects of HGF on Liver Fibrosis of Rats Induced with Dimethylnitrosamine 1. Test Method
  (1) Animals used: Wistar male rat, 5 weeks old
  (2) Test schedule Dimethylnitrosamine (DMN) was administered intraperitoneally to rats at a dose of 10 µl/kg on every Tuesday, Wednesday, Thursday over 4 weeks. HGF was administered intravenously to the rats at a dose of 500 µg/kg twice a day (1000 µg/kg/day) for 28 days from the first DMN administration. The administration schedule is shown in FIG. 1. On the 29th day, the test rats were subjected to the following measurement.

(3) Measurement

The rats were dissected to measure the weight of the liver. Further, the hydroxyproline content (Hyp; an index for fibrosis) and collagenase (collagen decomposition enzyme) activity in liver tissue were measured respectively by the method of Kivirikko et al. (Anal. Biochem, 19, 249, 1967) and the method of Murawaki et al. (J. Biochem, 108, 241, 1990). Further, DNA and protein contents in liver tissue were measured respectively by the Dishe method modified by Burton (Biochem, J, 62, 315, 1956) and Protein assay kit (manufactured by Bio-Rad Ltd.). The results are shown in Table 1.

Also, blood was collected from postcava at the same time, and the clinical biochemical test of the collected serum was analyzed by a Hitachi 7150 type automatic analysis apparatus. Then, using the EDTA-added blood collected from postcava, platelet number, leucocyte number, erythrocyte number, hematocrit value, hemoglobin concentration were measured by a multi item automatic blood cell counting apparatus (E-4000, manufactured by Sysmex). Also, using the plasma obtained by mixing 3.8% aqueous sodium citrate solution and the blood collected from postcava in a ratio of 1:9, the plasma coagulation ability (prothrombin time, fibrinogen content, coagulation time by the hepaplastein test and the thrombo test) was measured by an automatic coagulation ability measuring apparatus (KC-40). The result is shown in Table 2.

TABLE 1

|  | Solvent administered group | HGF administered group | normal animals |
|---|---|---|---|
| Liver weight (g) | 9.33 ± 0.72 | 13.02 ± 0.53** | 13.59 ± 0.51** |
| Total DNA content (mg/liver) | 33.6 ± 2.5 | 39.3 ± 1.8* | 44.8 ± 1.7** |
| Total protein content (g/liver) | 1.36 ± 0.12 | 1.84 ± 0.09** | 2.33 ± 0.09** |
| Collagenase activity (µg/min/g-liver) | 0.22 ± 0.01 | 0.36 ± 0.07** | 0.27 ± 0.02 |

TABLE 1-continued

|  | Solvent administered group | HGF administered group | normal animals |
|---|---|---|---|
| Hydroxyproline content (µg/g-liver) | 423.1 ± 35.9 | 300.1 ± 18.0** | 129.3 ± 6.4** |

Average ± standard error (n = 10)
*: $P < 0.05$, **: $P < 0.01$ vs. solvent administered group

TABLE 2

|  | Solvent administered group | HGF administered group | normal animals |
|---|---|---|---|
| Serum biochemistry test value |  |  |  |
| GOT (IU/l) | 136 ± 9 | 78 ± 4** | 64 ± 3** |
| GPT (IU/l) | 50 ± 4 | 28 ± 1** | 15 ± 1** |
| γ-GTP (U/l) | 4.8 ± 0.4 | 3.4 ± 0.2** | 1.9 ± 0.1** |
| Total bilirubin (mg/dl) | 0.45 ± 0.08 | 0.25 ± 0.01** | 0.19 ± 0.01** |
| Direct bilirubin (mg/dl) | 0.20 ± 0.02 | 0.18 ± 0.00 | 0.13 ± 0.01** |
| Total protein (g/dl) | 4.9 ± 0.1 | 6.4 ± 0.1** | 5.7 ± 0.0** |
| Albumin (g/dl) | 2.4 ± 0.1 | 3.1 ± 0.1** | 2.6 ± 0.0** |
| Blood sugar (mg/dl) | 131 ± 4 | 152 ± 6** | 180 ± 8** |
| Total cholesterol (mg/dl) | 53 ± 2 | 98 ± 5** | 72 ± 3** |
| HDL-cholesterol (mg/dl) | 28.0 ± 1.9 | 61.6 ± 3.9** | 41.3 ± 1.7** |
| Triglyceride (mg/dl) | 70 ± 9 | 152 ± 16** | 157 ± 16** |
| Phospholipid (mg/dl) | 116 ± 4 | 208 ± 8** | 160 ± 5** |
| β-lipoprotein (mg/dl) | 107 ± 11 | 222 ± 20** | 202 ± 18** |
| Blood, coagulation test value |  |  |  |
| Platelet number ($10^4$/µl) | 31 ± 5 | 78 ± 4** | 105 ± 5** |
| Leukocyte number ($10^2$/µl) | 144 ± 6 | 101 ± 8** | 87 ± 8** |
| Erythrocyte number ($10^4$/µl) | 667 ± 16 | 702 ± 9** | 755 ± 6** |
| Hematocrit value (%) | 39.9 ± 0.9 | 41.6 ± 0.3* | 44.3 ± 0.3** |
| Hemoglobin concentration (g/l) | 12.7 ± 0.3 | 13.6 ± 0.1** | 14.6 ± 0.1** |
| Prothrombin time (sec) | 15.6 ± 0.5 | 13.8 ± 0.2* | 13.8 ± 0.2* |
| Fibrinogen (g/dl) | 1.45 ± 0.10 | 2.05 ± 0.11** | 2.31 ± 0.05** |
| Hepaplastein time (sec) | 37.3 ± 2.7 | 28.6 ± 0.6** | 28.5 ± 0.5** |
| Thrombo test time (sec) | 30.0 ± 1.9 | 22.5 ± 0.3** | 22.8 ± 0.3** |

Average ± standard error (n = 10)
*: $P < 0.05$, **: $P < 0.01$ vs. solvent administered group 2. Result As shown in Table 1 and Table 2, owing to repeated administration of DMN, remarkable progression of the liver fibrosis and shrink of the liver were observed in the solvent administered group (control), and clear depression in the liver function was confirmed by the clinical biochemistry, blood and coagulation test values. On the other hand, liver function test values of the HGF administered group manifested values near normal animals with significant difference as compared with those values of the solvent administered group, and revealed clear improving effect. Further, because of HGF administration, collagenase activity, protein and DNA content in the liver tissue significantly increased, the hydroxyproline content which is the index of fibrosis significantly decreased, and the liver weight was recovered to approximately normal level.

Example 2

Action of HGF on Liver Fibrosis of Rats Induced with Carbon Tetrachloride

Carbon tetrachloride was administered orally to Wister male rats (6 weeks old) at a dose of 0.7 ml/kg on every Monday and Thursday for 12 weeks to prepare liver fibrosis models. These rats with liver fibrosis induced with carbon tetrachloride were subjected to the following two tests.

(1) Test A
Repeated Administration Test

Figure 2:
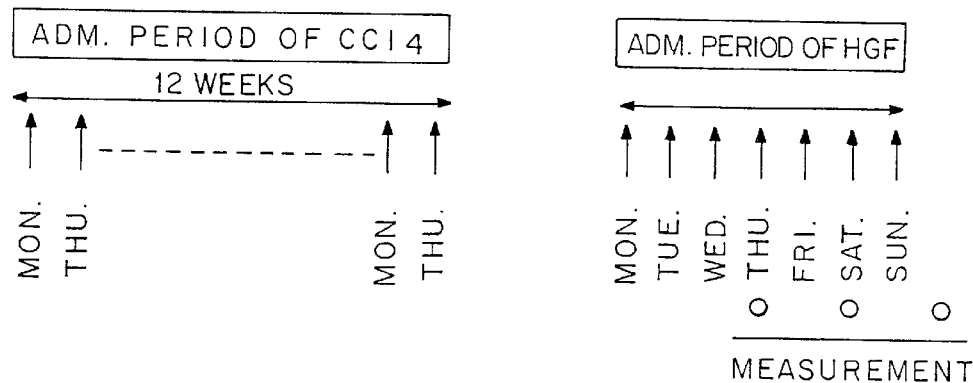
FIG. 2 is a chart which shows medicine-administration schedule in Test A of Example 2.

HGF was administered intravenously to the above-described rats with liver fibrosis induced with carbon tetrachloride (one group includes 13–14 individuals) at doses of 50 and 500 µg/kg twice a day (100 and 1000 µg/kg/day) for 7 days. The administration schedule is shown in FIG. 2. The changes of GOT, GPT and γ-GTP values in the serum on day 3, 5 and 7 after the initiation of HGF administration were compared with those in the serum of solvent administered group (control). The results are shown in FIGS. 4A–4C.

Figure 4A:
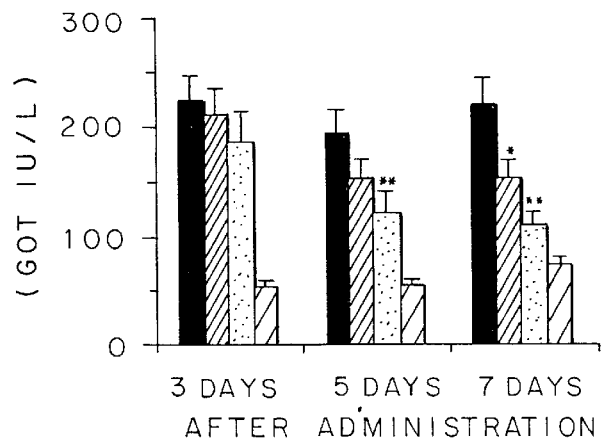
FIGS. 4A–4C are graphs showing the results of GOT (FIG. 4A), GPT (FIG. 4B) and γ-GTP (FIG. 4C) measurements in Test A of Example 2.
Figure 4B:
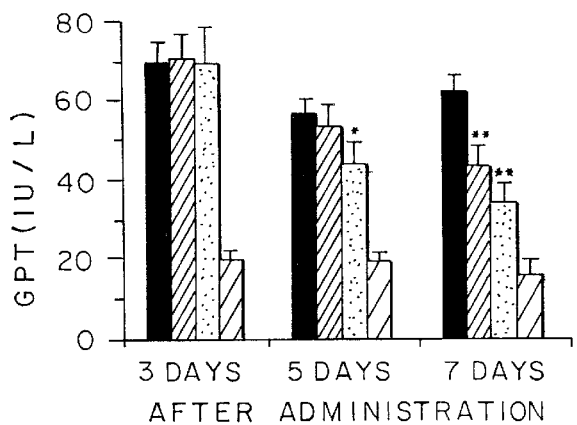
Figure 4C:
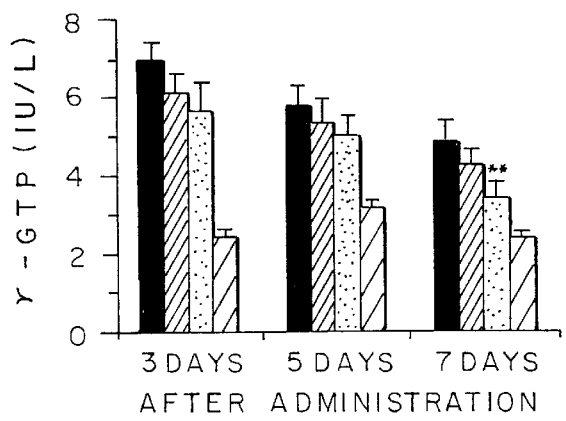
Figure 5A:
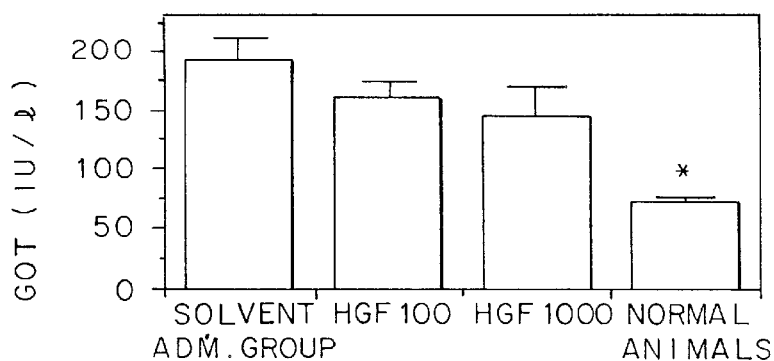
FIGS. 5A–5D are graphs showing the results of GOT (FIG. 5A), GPT (FIG. 5B) and hepaplastin tests (FIG. 5C) and the measurement of liver Hyp (hydroxyproline) (FIG. 5D) content in Test B of Example 2.
Figure 5B:
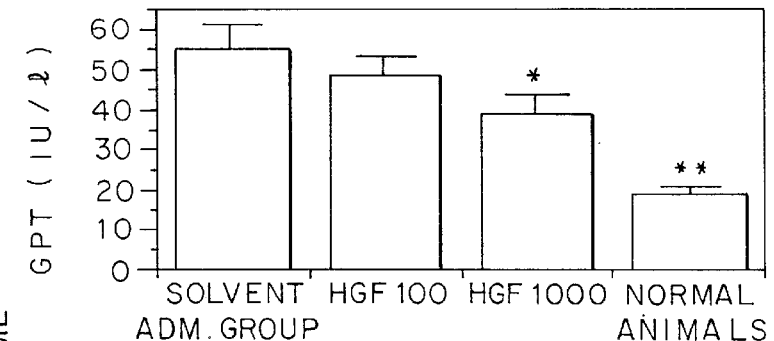
Figure 5C:
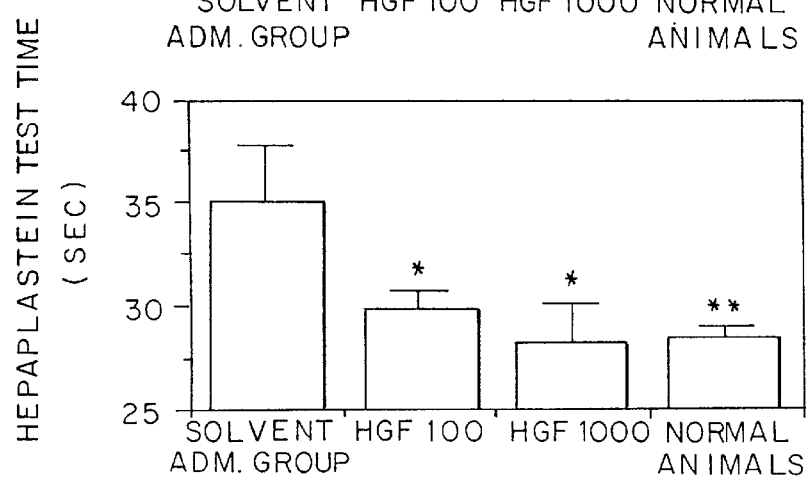
Figure 5D:
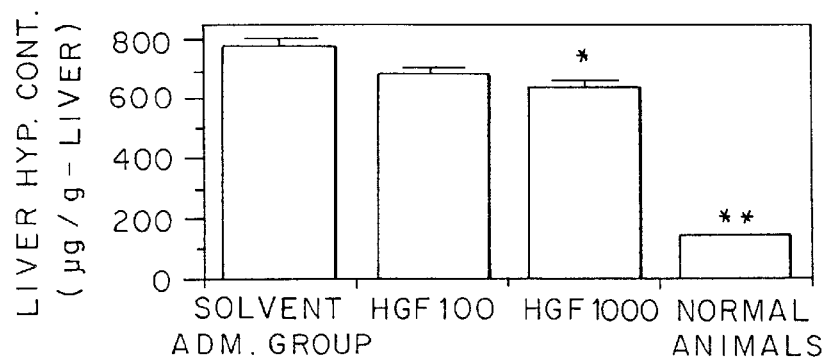

As shown in FIGS. 4A–4C, accelerating effect of HGF on recovery was observed on day 5 at a dose of 100 µg/kg/day and on day 7 at a dose of 100 µg/kg/day.

(2) Test B
Drip Injection Test

Figure 3:
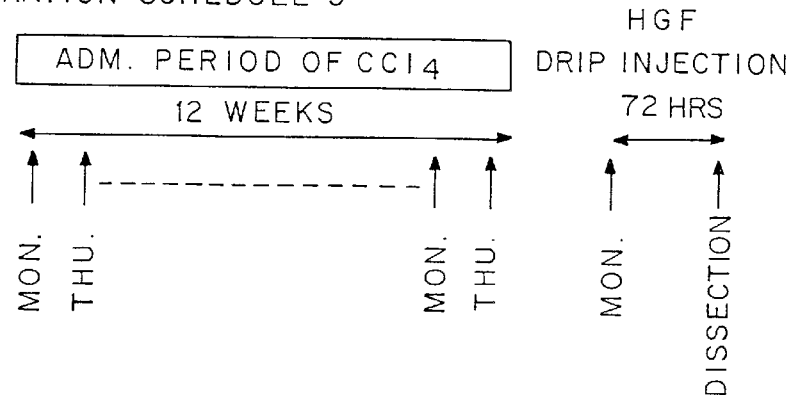
FIG. 3 is a chart which shows medicine-administration schedule in Test B of Example 2.

HGF was infused into the above-described rats with liver fibrosis induced with carbon tetrachloride (n=12–13 per group) at doses of 100 and 1000 µg/kg/day through a catheter indwelt in cervical vein, and they were dissected 72 hours after the initiation of HGF infusion. The HGF infusion schedule is shown in FIG. 3.

GOT, GPT, serum total protein, albumin in the serum were measured by a Hitachi 7150 type automatic analysis apparatus, and with respect to the coagulation ability of the plasma obtained by mixing 3.8% aqueous sodium citrate solution and the blood collected from postcava in a ratio of 1:9, the coagulation time in the hepaplastein test was measured by an automatic coagulation ability measuring apparatus (KC-40). Further, the hydroxyproline content in liver tissue (Hyp) which is the index of fibrosis was measured by the above-described method of Kivirikko et al. The results are shown in Table 3 and FIGS. 5A–5D.

As shown in Table 3 and FIGS. 5A–5D, when HGF was administered at a dose more than 100 µg/kg/day, there were observed the improvement of the liver function test value, the recovery in hypoproteinemia and reduction of the hydroxyproline content in liver tissue which indicates improvement of fibrosis, each depending on the doses.

TABLE 3

|  | Total protein conc. (g/dl) | Albumin conc. (g/dl) |
|---|---|---|
| Solvent administered group | 5.0 ± 0.1 | 1.8 ± 0.1 |
| HGF administered group (100 µg/kg/day) | 5.5 ± 0.2* | 2.1 ± 0.1* |
| HGF administered group (1000 µg/kg/day) | 5.7 ± 0.2** | 2.1 ± 0.1* |
| Healthy and normal animals | 6.0 ± 0.1** | 2.4 ± 0.03** |

Average ± standard error (n = 12 to 13)
*: $P < 0.05$, **: $P < 0.01$ vs. solvent administered group

Example 3

Effect of HGF on Liver Fibrosis of Rats Induced with DMN and on Accompanied Liver Function Insufficiency (1) Test A The HGF-administered group and HGF-unadministered group of the rats with liver fibrosis induced with DMN were tested for their survival ratios.

Figure 6:
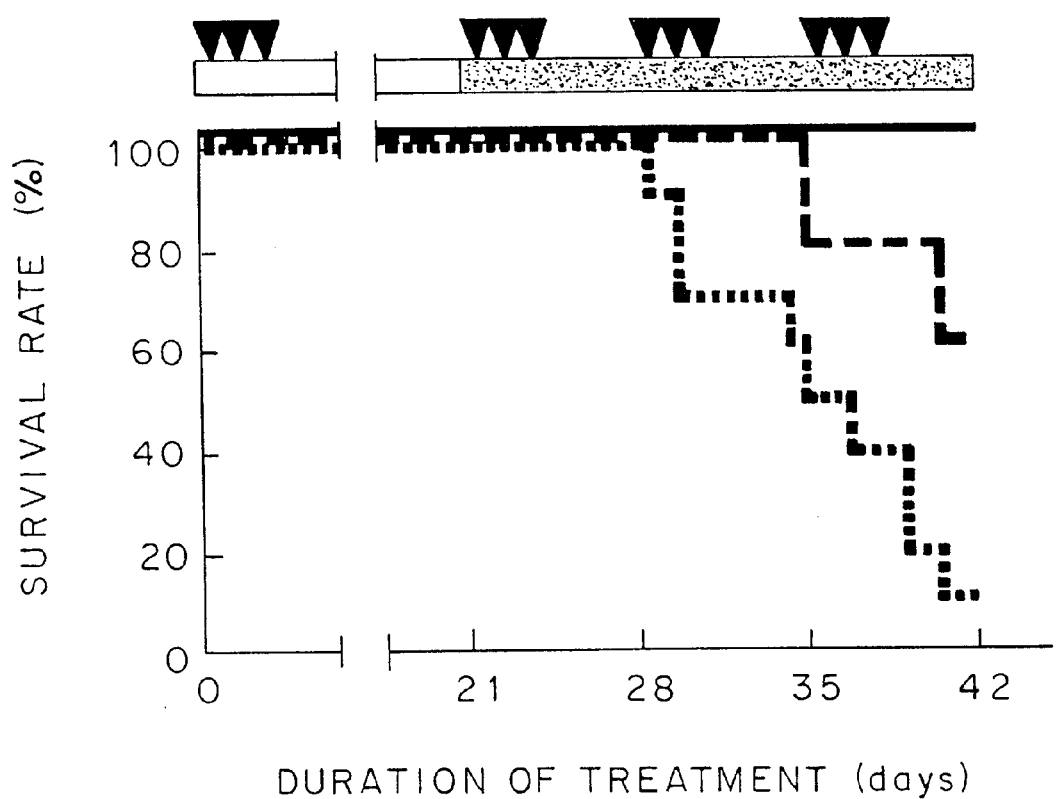
FIG. 6 is a graph which shows the survival effect of HGF on a liver fibrosis of rats in Test A of Example 3.
Figures 7A, 7B, 7C, 7D:
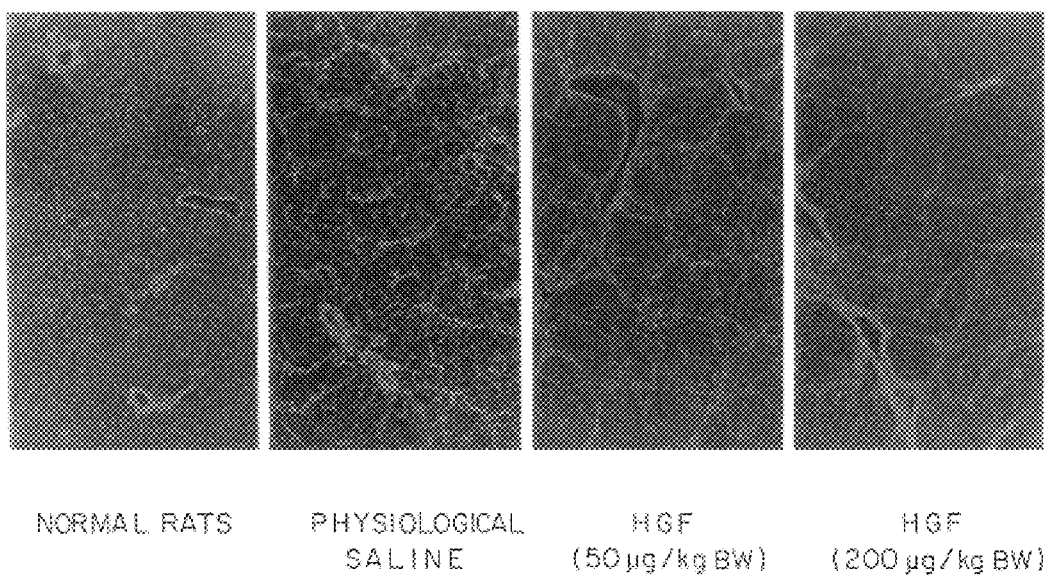
FIGS. 7A–7D are photographs which shows the liver-fibrosis relieving effect of HGF on rats with liver fibrosis in Test B of Example 3.

The administration schedule of medicines is shown in upper portion of FIG. 6. DMN dissolved in a physiological saline in a concentration of 1% was administered intraperitoneally to SD male rats three times a week for 6 weeks as indicated by arrows at a dose of 10 µl of DMN per 1kg body weight. The human HGF or the physiological saline was administered intravenously to rats every day for the period shown by a hatched band from the 21st day after the initiation of DMN administration, to examine the time course of survival rates of tested rats. The results are shown in FIG. 6. In the FIG. 6, the dotted line indicates the physiological saline administered group (control group, n=10), the broken line indicates a HGF 50 µg/kg body weight administered group (n=5), and the solid line indicates a HGF 200 µg/kg body weight administered group (n=5).

As shown in FIG. 6, by the administration of HGF, the survival rates were improved, and especially, no death was observed in the HGF 200 µg/kg body weight administered group.

(2) Test B

The type I collagen deposition (histological observation) of the liver of the DMN administered rat was examined under administration or non-administration of HGF.

Namely, for detection of collagen fibers, the rats were sacrificed and the livers were taken out on the 42nd day in the tests shown in FIG. 6. For the immunofluorescent stain of collagen, the liver was quickly frozen in OTC compound, and the prepared slices were reacted with a rabbit anti rat collagen type I antibody (obtained from LSL Ltd.) and a fluorescent-labeled goat anti rabbit IgG antibody, then the specimens were photographed. The results are shown in FIGS. 7A–7D.

As shown in FIGS. 7A–7D, there was a significant difference between administration and non-administration of HGF in depositions of type I collagen in the liver. In control rat group administrated the physiological saline, the deposition of type I collagen in the liver was evident, thick or thin bundles of a type I collagen fiber were deposited in the wide range around blood vessels and hepatocytes.

These events disappeared by the administration of HGF in a dose-dependent manner, the improvement of lobulus structure was remarkable in the HGF administered group. In this way, the preventing effect of HGF on liver fibrosis was demonstrated by the histological observation of the liver section.

(3) Test C

The changes in prothrombin time, hepatocyte-leaked enzyme and hepatic hydroxyproline contents by HGF administration were examined.

Namely, rats were treated according to the experiment scheme shown in FIG. 6. Prothrombin time (PT), values in serum (plasma) of albumin (Alb), glutamic-oxaloacetic transaminase (GOT), glutamic-pyruvic transaminase (GPT) and alkaline phosphatase (ALP), and liver hydroxyproline content (HYP) were measured respectively in a normal rat group (n=5, indicated as normal rat in Table 4), a group in which DMN treatment had been conducted for 5 weeks and only physiological saline had been administered (n=5, indicated as 5W in Table 4), a group in which DMN treatment had been conducted for 6 weeks and only physiological saline had been administered (n=5, indicated as 6W in Table 4) or groups in which HGF was administered at doses of 50 µg/kg body weight (n=3, indicated as 50 in Table 4) and 200 µg/kg body weight (n=5, indicated as 200 in Table 4) instead of the physiological saline. The results are shown in Table 4. Here, the values indicated as 5W were obtained by sacrificing rats on the 35th day, and the other values were obtained by sacrificing rats on the 42nd day after the initiation of the DMN treatment.

As shown in Table 4, owing to HGF administration, it was noticed that the liver fibrosis and liver function insufficiency were improved.

TABLE 4

| | | | PT (sec.) | Alb (mg/dl) | GOT (IU/L) | GPT (IU/L) | ALP (IU/L) | HYPRO (μg/g Liver) |
|---|---|---|---|---|---|---|---|---|
| Normal rat | | (n = 5) | 14.2 ± 2.7 | 4.5 ± 0.04 | 76 ± 16 | 19 ± 3 | 459.6 ± 65 | 224 ± 89 |
| Physialogical | 5W | (n = 5) | — | — | 314 ± 71 | 132 ± 16 | 1967 ± 236 | 740 ± 211 |
| saline | 6W | (n = 1) | 80< | 2.6 | 162 | 49 | 1268 | 1011 |
| H G F | 50 | (n = 3) | 32.0 ± 11.2 | 2.6 ± 0.8 | 165 ± 38 | 42 ± 14 | 1081 ± 523 | 789 ± 58 |
| | 200 | (n = 5) | 21.4 ± 5.2 | 3.1 ± 0.7 | 164 ± 38 | 40 ± 12 | 1053 ± 448 | 666 ± 116 |

Example 4

Effect of HGF Administration on Improvement of Liver Fibrosis of Rats Induced with DMN (1) Method DMN was administered intraperitoneally to SD male rats (5 weeks-old) at a dose of 10 μl/kg three consecutive days a week (Monday, Tuesday, Wednesday) for 4 weeks to make rats with liver fibrosis. To these rats was administered 1 mg/kg of HGF or 1 ml/kg of a solvent (phosphate buffered saline comprising 2.5 mg/ml of HSA and 0.01% of Tween 80) five consecutive days a week (Monday, Tuesday, Wednesday, Thursday, Friday) from the initiation of DMN administration to the 4th day of the 4th week. On the 5th day of the 4th week, the rats were sacrificed, the livers were taken out and fixed in neutral formalin, and after preparation of sections, they were subjected to Masson's trichrome staining which stains fiber tissue and does not stain other tissue. Here, for comparison, the livers of normal rats were likewise stained. With respect to the liver tissue specimens of respective individuals, the area of fibrous tissue in the total area of the tissue section was calculated respectively by an image analysis apparatus (T. Watanabe et al. Analytical Cellular Pathology 4 (3), 248, 1992), and the degrees of fibrous tissue in normal tissue were compared. The samples used for the analysis includes 8 specimens of the normal rats, 8 specimens of the DMN+solvent administered group, and 6 examples of the DMN+HGF administered group (HGF+DMN) except for specimens of rats in which the neutralization activity for HGF was generated in their serum.

(2) Result

Figure 8:
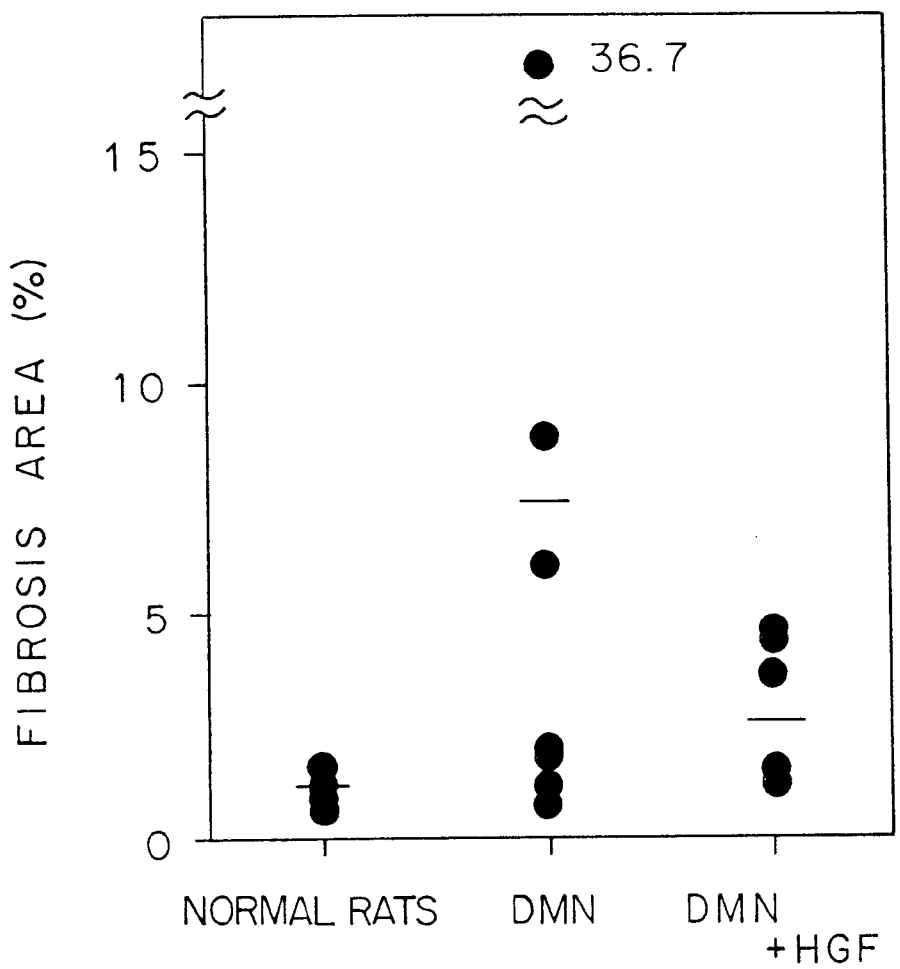
FIG. 8 is a graph which shows the proportion (%) of fibrous tissue of an each individual liver in Example 4.

The results are shown in FIG. 8. Each point in the figure indicates the ratio (%) of fibrous tissue in an each individual liver of normal rats (n=8), DMN administered rats (n=8) or DMN+HGF administered rats (n=6). The horizontal bar indicates the average value.

As shown in FIG. 8, as compared with normal rats, the ratio of fibrous tissue in liver tissue of the DMN administered group increased to 7.3% from 1.3% (average, normal rats). On the other hand, in the case of the DMN+HGF administered group, the ratio decreased to 2.8% compared to that in the DMN administration group. This phenomenon indicates the improvement of liver fibrosis induced with DMN by administration of HGF.

What is claimed is:

1. A method for treating fibrosis disorder caused by excessive collagen deposition comprising administering to a subject in need thereof a hepatocyte growth factor in an amount effective to accelerate collagen decomposition.

\* \* \* \* \*